(12) United States Patent
Vogt et al.

(10) Patent No.: US 9,833,472 B2
(45) Date of Patent: Dec. 5, 2017

(54) ANTISEPTIC POLYMETHYLMETHACRYLATE BONE CEMENT

(71) Applicant: HERAEUS MEDICAL GMBH, Wehrheim (DE)

(72) Inventors: Sebastian Vogt, Erfurt (DE); Klaus-Dieter Kühn, Marburg (DE)

(73) Assignee: HERAEUS MEDICAL GMBH, Wehrheim (DE)

( * ) Notice: Subject to any disclaimer, the term of this patent is extended or adjusted under 35 U.S.C. 154(b) by 52 days.

(21) Appl. No.: 14/081,180

(22) Filed: Nov. 15, 2013

(65) Prior Publication Data

US 2014/0141097 A1 May 22, 2014

(30) Foreign Application Priority Data

Nov. 16, 2012 (DE) .................. 10 2012 022 419

(51) Int. Cl.
  C08L 33/12 (2006.01)
  A61K 33/40 (2006.01)
  A61L 24/00 (2006.01)

(52) U.S. Cl.
  CPC .......... *A61K 33/40* (2013.01); *A61L 24/0015* (2013.01); *A61L 2300/11* (2013.01); *A61L 2430/02* (2013.01); *C08L 33/12* (2013.01); *C08L 2312/00* (2013.01)

(58) Field of Classification Search
  None
  See application file for complete search history.

(56) References Cited

U.S. PATENT DOCUMENTS

| | | | |
|---|---|---|---|
| 3,349,047 A * | 10/1967 | Sheard | C08L 81/00 524/788 |
| 3,629,331 A | 12/1971 | Kabacoff et al. | |
| 4,150,485 A * | 4/1979 | Lee, Jr. | A61K 6/083 252/301.6 R |
| 4,849,223 A | 7/1989 | Pratt et al. | |
| 5,266,609 A * | 11/1993 | Hall | A61K 6/0023 523/116 |
| 6,984,392 B2 | 1/2006 | Bechert et al. | |
| 8,512,762 B2 | 8/2013 | Vogt et al. | |
| 8,598,251 B2 | 12/2013 | Vogt et al. | |
| 8,829,073 B2 | 9/2014 | Nies | |
| 2002/0022677 A1 | 2/2002 | Teramae et al. | |
| 2003/0165556 A1 | 9/2003 | Bechert et al. | |
| 2006/0018943 A1 | 1/2006 | Bechert et al. | |
| 2006/0275339 A1 | 12/2006 | Schilke et al. | |
| 2007/0032568 A1* | 2/2007 | Lin | A61K 6/083 523/116 |
| 2007/0087031 A1 | 4/2007 | Ashman et al. | |
| 2008/0194729 A1 | 8/2008 | Nies | |
| 2009/0010981 A1 | 1/2009 | Bechert et al. | |
| 2009/0105366 A1 | 4/2009 | Vogt et al. | |
| 2009/0305983 A1 | 12/2009 | Ying et al. | |
| 2009/0324668 A1 | 12/2009 | Kangasniemi et al. | |
| 2010/0159027 A1 | 6/2010 | Vogt et al. | |
| 2011/0054392 A1 | 3/2011 | Nies | |
| 2011/0182995 A1 | 7/2011 | Asgary | |
| 2011/0183932 A1 | 7/2011 | Vogt et al. | |
| 2011/0287067 A1 | 11/2011 | Stewart | |
| 2011/0313078 A1 | 12/2011 | Vogt et al. | |
| 2013/0157901 A1* | 6/2013 | Ogle | C08F 2/38 507/119 |

FOREIGN PATENT DOCUMENTS

| | | |
|---|---|---|
| CN | 1826146 A | 8/2006 |
| CN | 100998889 A | 7/2007 |
| CN | 101496909 A | 8/2009 |
| CN | 102327642 A | 1/2012 |
| DE | 681205 C | 9/1939 |
| DE | 687217 C | 1/1940 |
| DE | 1169901 B | 5/1964 |
| DE | 10 2005 023 094 A1 | 11/2006 |
| DE | 10 2007 050 762 B3 | 5/2009 |
| DE | 10 2010 005 956 B4 | 9/2011 |
| DE | 10 2010 024 653 A1 | 12/2011 |
| EP | 0 190 504 A2 | 3/1986 |
| EP | 1 313 518 | 5/2003 |

(Continued)

OTHER PUBLICATIONS

Webb et al. J Bone Joint Surg Br vol. 89-B No. 7 p. 851-857.Jul. 2007.*
Shiramizu et al. vol. 9, Issue 1, pp. 17-22 Mar. 2008.*
First Chinese Office Action in corresponding application CN 201310571130.6 dated Feb. 2, 1015 and English translation.
Penner et al, "Elution characteristics of vancomycin and tobramycin combined in acrylic bone-cement"; The Journal of Arthroplasty, vol. 11, No. 8, 1996, pp. 939-944.
English translation of Decision of Rejection dated Dec. 15, 2015 in corresponding Japanese Patent Application No. 2013-227629.
English translation of Notice of Reason for Rejection dated Dec. 20, 2016 in corresponding Japanese Patent Application 2016-071555.

(Continued)

*Primary Examiner* — Nissa Westerberg
(74) *Attorney, Agent, or Firm* — Norris McLaughlin & Marcus, P.A.

(57) ABSTRACT

The invention proposes an antiseptic composition for use as bone cement, in particular an antiseptic polymethylmethacrylate bone cement, that can be cured and comprises a content of at least one component that is a compound with an oxidizing effect or from which a compound with an oxidizing effect can be released. Preferably, hydrogen peroxide is or can be released. In this context, it is particularly preferred to use an adduct or a salt of hydrogen peroxide that releases hydrogen peroxide in the presence of water or aqueous conditions. The antiseptic polymethylmethacrylate bone cement can be used for mechanical fixation of primary total articular endoprostheses, for mechanical fixation of revision total articular endoprostheses, and for producing spacers.

28 Claims, No Drawings

(56) References Cited

FOREIGN PATENT DOCUMENTS

| | | |
|---|---|---|
| EP | 1 648 531 | 4/2006 |
| EP | 2 198 893 A2 | 6/2010 |
| JP | 2001-302429 A | 10/2001 |
| JP | 2006 528008 A | 12/2006 |
| JP | 2008 007439 A | 1/2008 |
| JP | 2010 144168 A | 7/2010 |
| JP | 2010-522591 A | 7/2010 |
| WO | 82 01990 A1 | 6/1982 |
| WO | 02 017984 A1 | 7/2002 |
| WO | 2005 009495 A1 | 2/2005 |

OTHER PUBLICATIONS

Notice of Reasons for Rejection issued in JP Application No. 2013-227629 dated Jan. 27, 2015 and English translation.

* cited by examiner

ANTISEPTIC POLYMETHYLMETHACRYLATE BONE CEMENT

This application claims priority of German Patent Application No. 10 2012 022 419.2, filed Nov. 16, 2012, the entire contents of which are incorporated herein by reference.

The invention proposes an antiseptic composition for use as bone cement, in particular an antiseptic polymethylmethacrylate bone cement, that can be cured and comprises a content of at least one component that is a compound with an oxidising effect or from which a compound with an oxidising effect can be released. Preferably, hydrogen peroxide is or can be released. In this context, it is particularly preferred to use an adduct or a salt of hydrogen peroxide that releases hydrogen peroxide in the presence of water or aqueous conditions. The antiseptic polymethylmethacrylate bone cement can be used for mechanical fixation of primary total articular endoprostheses, for mechanical fixation of revision total articular endoprostheses, and for producing spacers.

A subject matter of the invention is an antiseptic polymethylmethacrylate bone cement. Said cement is intended, in particular, for producing spacers (temporary placeholders) in the scope of the two-stage septic revision of articular total endoprostheses (TEP).

Articular total endoprostheses are used widely to preserve articular function, mainly in the knee or hip joint. Shoulder TEPs and elbow TEPs are also used, though to a lesser extent. The TEPs can be anchored in the bony implant bed by means of polymethylmethacrylate bone cement or by press-fit in the case of cement-free prostheses.

Unfortunately, despite modern hygiene and surgical techniques, the implantation of TEPs is still associated with a very low number of infections of the bone and soft tissue surrounding the TEP. Here, early and late infections need to be distinguished. Early infections are often caused by pathogens that enter the human tissue during the implantation of the TEP. In late infections, usually some haematogenic dissemination of pathogens is being discussed. Said infections are a very serious complication for the patient. In extreme cases, TEP-associated infections can lead to chronic osteitis and even to life-threatening sepsis in very extreme cases.

TEP-associated infections are treated mainly by one-stage and two-stage TEP revisions. What is essential in either case is that the infected tissue is removed radically in the scope of a debridement. In one-stage TEP revision, the primary TEP is explanted and a radical debridement is performed right away and then the revision TEP is mechanically fixed in the debrided bony implant bed right away using an antibiotics-doped polymethylmethacrylate bone cement. In two-stage TEP revision, a first surgery is used to remove the infected primary TEP, followed by debridement of the infected tissue and then a temporary placeholder consisting of polymethylmethacrylate (spacer) containing an antibiotic, or in most cases two or more antibiotics, is implanted. Said spacer replicates the primary TEP that has been removed and serves for what is called dead-space management. This means that the spacer prevents the formation of extensive haematomas that may favour recurrence and largely prevents atrophy of the muscles and tendon system. Moreover, the antibiotic-doped spacer continuously releases the antibiotics present therein to the surrounding tissue. Any residual microbial pathogens that may still be present in the surrounding tissue and, mainly, on the surface of the spacer are thus controlled effectively. Approx. 4-6 weeks after implantation of the spacer, it is customary to biopsy the joint and to test the biopsy specimen for the presence of microbial pathogens. Typical clinical inflammation markers, such as CRP, reddening, swelling, and temperature increase are detected as well on this occasion. Once it has been determined that the infection is subsiding, a second surgery is performed to remove the spacer and perform another debridement. Subsequently, the revision TEP is implanted using no cement or polymethylmethacrylate bone cement.

It is common to add combinations of antibiotics to the cement powder during spacer production, whereby the antibiotics are selected to match the causative microbial pathogens of the infection (L. Frommelt: Lokale Antibiotikatherapie. In: Septische Knochenchirurgie. Eds. R. Schnettler, H.-U. Steinau, Georg Thieme Verlag Stuttgart New York 2004, 82-90). It is customary to use combinations of two to four antibiotics in this context. However, the use of antibiotics has been the subject of controversial debate due to the formation of resistance. It is advantageous though that many of the relevant antibiotics, for example gentamicin and vancomycin, can be excreted renally in virtually unmodified form by the human body.

There have been attempts to incorporate antiseptics instead of antibiotics into polymethylmethacrylate bone cements.

Accordingly, WO 8201990 A1 proposed a bone cement that contains up to 5% by weight silver salts. An antimicrobial composition containing up to 10% by weight elemental silver and, in addition, titanium dioxide or tantalum oxide was disclosed in U.S. Pat. No. 4,849,223 A. EP 1313518 A1 described a bone cement containing silver particles of 20 µm in size. Said silver particles are made up of smaller silver particles of a size in the nanometer range.

The use of elemental silver or silver salts is an issue since the silver ions, which are actually meant to act microbicidal, are non-selective and interact not only with microbial structures, but with human tissue structures as well. Accordingly, poorly water-soluble salts can be formed with cysteine and cysteine-containing proteins. Moreover, silver ions can react with phosphate ions to form poorly soluble silver orthophosphate. It must be presumed that silver compounds introduced into the human body can basically not be eliminated, as is evident from the long-known phenomenon of argyrosis, i.e. irreversible skin changes due to silver.

EP 1648531 A1 disclosed a polymethylmethacrylate bone cement containing cationic antiseptics, whereby polyhexamethylenebiguanide is particularly preferred as the antiseptic. However, an issue to be discussed in this context is that said cationic antiseptics cannot be degraded by human tissue and there is a risk of local accumulation.

The invention is based on the object to develop a bone cement, preferably a polymethylmethacrylate bone cement, which, after an implantation, releases a broad range antiseptic upon the influence of body fluids, whereby the antiseptic is to show not only a strong temporary microbicidal effect, but also should or must not accumulate in human tissue in order to prevent adverse toxic effects. Moreover, the antiseptic is to be released in delayed manner, if possible.

The object of the invention was met as described hereinbelow.

The invention is based on the rationale to introduce at least one hydrogen peroxide compound into a composition for use as bone cement, such as a polymethylmethacrylate bone cement, whereby the hydrogen peroxide compound is capable of releasing hydrogen peroxide under defined conditions as a compound with an oxidising effect, preferably by delayed release. In this context, it is particularly preferred to introduce a hydrogen peroxide adduct and/or salt into the polymethylmethacrylate bone cement. Preferred adducts and salts release hydrogen peroxide when exposed to the influence of water or aqueous solutions, such as aqueous conditions inside the body. Hydrogen peroxide is a broad-range antiseptic that has a strong microbicidal effect due to its oxidising effect. It is particularly advantageous that hydrogen peroxide cannot accumulate in the human body, since the human body contains catalases and peroxidases that degrade hydrogen peroxide. The particular advantage of the composition according to the invention or the bone cement according to the invention is that it prevents the formation of resistance by the micro-organisms which can happen with antibiotics-based therapies. Another advantage of the use according to the invention is that the antiseptic effect stays very local, since the afore-mentioned catalases and peroxidases can degrade the hydrogen peroxide formed.

A subject matter of the invention is a composition for use as bone cement, in particular a polymethylmethacrylate bone cement, whereby the composition is curable and comprises a content of at least one component that is a compound having an oxidising effect or from which a compound having an oxidising effect can be released, whereby the oxidising compound is released from the component in the presence of water. Another subject matter of the invention is the use of at least one compound having an oxidising effect in an antiseptic bone cement. Preferably, the compound having an oxidising effect is released from the component in the form of hydrogen peroxide in the presence of $H_2O$, such as moisture, water or in aqueous conditions of a body fluid. For this reason, compounds having an oxidising effect according to the invention include hydrogen peroxide or compounds that contain at least one peroxy group (—O—O—) and react with water while releasing hydrogen peroxide ($H_2O_2$, H—O—O—H).

According to the invention, the composition is an antiseptic polymethylmethacrylate bone cement.

A broad-range antiseptic, the hydrogen peroxide that is released in delayed manner can reduce surface pathogens on spacers or endoprostheses and is in turn degraded in the body by catalase (gene name: CAT), an enzyme that converts hydrogen peroxide ($H_2O_2$) to form oxygen ($O_2$) and water ($H_2O$). By this means, the antimicrobial efficacy is limited locally to the region of the implant, spacer or endoprosthesis and does not accumulate in the body of the patient.

Another subject matter of the invention is a composition for use as bone cement, in particular a polymethylmethacrylate bone cement, whereby the composition is curable and releases hydrogen peroxide or whereby hydrogen peroxide can be released and/or delivered from the composition. Particularly preferably, the hydrogen peroxide is released from the curable or cured composition by delayer release. Preferably and in particular, part of the hydrogen peroxide is released right away, i.e. within up to 4 or 6 weeks, in order to kill existing pathogens immediately, preferably followed by the release of lower concentrations, if applicable, over the subsequent period of time, whereby the concentration may continue to decrease.

Also a subject matter of the invention is a composition for use as bone cement, in particular a polymethylmethacrylate bone cement, particularly preferably an antiseptic bone cement. In this context, the composition is curable and contains, preferably as a component, a hydrogen peroxide compound that is hydrogen peroxide or releases hydrogen peroxide. Preferably, the hydrogen peroxide compound is selected from hydrogen peroxide, a hydrogen peroxide adduct, a hydrogen peroxide complex, a hydrogen peroxide salt, a co-crystal including hydrogen peroxide, a hydrogen peroxide-releasing compound, such as, for example, a compound releasing hydrogen peroxide due to enzyme action, a solution containing solid hydrogen peroxide having a non-stoichiometric composition or a mixture containing at least two of the afore-mentioned compounds. According to the invention, the hydrogen peroxide can be released from the hydrogen peroxide compound, preferably after a curing process, such as by polymerisation of a liquid monomer and at least one organic polymer that is soluble in said monomer.

The afore-mentioned hydrogen peroxide compounds, preferably the afore-mentioned adducts, salts, complexes and/or co-crystals can, in general, be used independently of each other in the composition as polymorphs, hydrates, such as stoichiometric or non-stoichiometric hydrates, as solvates or in amorphous form. Using hydrogen peroxide salts or hydrogen peroxide adducts, complexes, or co-crystals, generally all pharmaceutically acceptable compounds or compounds approved according to the drug laws are suitable to be present as second molecular compound or as organic or inorganic ionic compound in the afore-mentioned hydrogen peroxide compounds. The cations of sodium, potassium, magnesium, calcium and/or zinc are preferred.

In general, pharmacologically acceptable compounds are used as hydrogen peroxide compounds in the composition, preferably in the bone cement. Pertinent examples include gluconate, maleate, etc.

The term, polymethylmethacrylate bone cement, shall be understood to refer to conventional cements, in which a polymer powder component and a liquid monomer component are mixed to form a self-curing cement dough through radical polymerisation. This term also includes pasty polymethylmethacrylate bone cements, in which two separate pre-swelled cement pastes are mixed to produce a self-curing cement dough. Examples include unexamined German patent applications DE 102007050762 B3, DE 102010024653 B4, and DE 102010005956 B4.

The composition according to the invention, which can be used as bone cement, preferably comprises at least a) hydrogen peroxide, a hydrogen peroxide adduct, a hydrogen peroxide complex or a hydrogen peroxide salt that releases hydrogen peroxide as compound having an oxidising effect in the presence of moisture, water, aqueous conditions or an aqueous solution, and/or b) a hydrogen peroxide compound that releases hydrogen peroxide in enzyme-catalysed manner. Therefore, according to an alternative, a hydrogen peroxide compound that releases hydrogen peroxide due to the presence of an enzyme can be used as hydrogen peroxide-releasing compound just as well.

An antiseptic polymethylmethacrylate bone cement comprising at least one hydrogen peroxide adduct or hydrogen peroxide salt that releases hydrogen peroxide in the presence of water, moisture, in aqueous solutions or aqueous conditions, in particular from the cured state, is particularly preferred according to the invention.

Furthermore, it is preferred not to use an acidic compound and no peroxy acid, such as peracetic acid, as hydrogen peroxide compound. However, generally, a salt of a peroxy acid can be used, such as an alkali or alkaline earth metal salt or zinc salt of peroxy acids that also act as buffers.

Components that are particularly preferred according to the invention, such as at least one hydrogen peroxide compound, comprise at least one urea-hydrogen peroxide adduct (CAS 124-43-6) and/or a sodium percarbonate (CAS 15630-89-4, an adduct of hydrogen peroxide and sodium carbonate).

According to an also preferred alternative, a hydrogen peroxide salt such as calcium peroxide (CAS 1305-79-9), calcium peroxide octahydrate (CAS 78403-22-2) and/or sodium peroxide (1313-60-6) or a mixture comprising the afore-mentioned is used as component, preferably as hydrogen peroxide compound. According to yet another also preferred alternative, a mixture comprising an urea-hydrogen peroxide adduct and calcium peroxide is used in the composition as component, in particular as hydrogen peroxide compound. The mixtures comprising urea-hydrogen peroxide adduct and calcium peroxide are particularly advantageous since the urea-hydrogen peroxide adduct releases hydrogen peroxide relatively rapidly in the presence of water. In contrast, calcium peroxide releases hydrogen peroxide more slowly in the presence of water. Not only hydrogen peroxide, but also calcium hydroxide is produced during this hydrolysis. Calcium hydroxide is a medium strength base that can be scavenged by means of buffer substances, in particular the alkali salts of buffer substances, for example while forming insoluble salts.

Combining hydrogen peroxide compounds having different, but defined hydrogen peroxide release profiles therefore allows the release rate, the duration of release, and the local concentration of hydrogen peroxide on the surface and/or in the tissue surrounding the cured composition, such as an implant or spacer, to be controlled very well and according to need.

To adjust the release of hydrogen peroxide as desired, the composition, in particular the bone cement, can contain 0.001 to 10% by weight, in particular 0.01 to 5% by weight, preferably from 0.01 to 2.5% by weight, more preferably between 0.01 and 1% by weight of the hydrogen peroxide compound, relative to the total composition. In this context, the composition can just as well be produced by mixing two or more pastes or a paste and a powder component, whereby the hydrogen peroxide compound can be present in one or both pastes and just as well in the powder composition. It is preferred in this context that the hydrogen peroxide compound is present in the composition at a content that corresponds to a content of approx. 0.01 to 5% by weight after curing. According to the invention, at least one hydrogen peroxide adduct or hydrogen peroxide salt is present in the cured polymethylmethacrylate bone cement in a range from 0.01 to 5% by weight, preferably between 0.01 to 1% by weight.

An adduct (http://goldbook.iupac.org/A00138.html)-Addukt is understood to be a chemical species AB that comprises molecules by direct combination of two separate molecules A and B in a manner formed by changes in possible connectivity, but without loss of atoms in molecules A and B. An adduct can have properties that differ from those of the separate molecules. The stoichiometry of adducts can be 1:1, but can also be any other conceivable stoichiometry, such as, for example, a bis-adduct (2:1) or 2:3 adduct, etc. An intramolecular adduct can be formed when groups A and B are present in the same molecular entity. Lewis adducts, π adducts, σ adduct or complexes are also known (http://goldbook.iupac.org/C01203.html). A complex is understood to be a molecular unit formed by loose association of two or more molecular compounds that can be ionic or uncharged. The term, electron donor-acceptor complexes, inter alia, is also known. A co-crystal is understood to be a crystalline compound, in which the stoichiometry of the participating molecules is fixed and which are usually formed through hydrogen bridge bonds or weak interactions, such as, for example, (π)C—H—O/N—, —(O)C—H—O/N— bonds.

For example pharmaceutically acceptable adducts of sodium acetate, sodium citrate, succinimide, asparagine, hexamethylene tetramine and further adducts of hydrogen peroxide and pharmaceutically acceptable molecules or salts can be used as hydrogen peroxide adducts.

Numerous proposals have been made in attempts to improve the stability on storage of hydrogen peroxide adducts; DE 681205 C proposed to impregnate the hydrogen peroxide-urea adduct with water-repelling agents, e.g. with fats or waxes. DE 687217 C described the addition of surface-active substances. According to U.S. Pat. No. 3,629,331 A, it is recommended to add ethylenediamine tetraacetic acid (EDTA) and sodium dihydrogenphosphate to the urea peroxide. Moreover, 3 to 9% by weight colloidal silica can be added to improve the flow properties. DE 1169901 B describes a method for producing hydrogen peroxide-containing pastes, in which hydrogen peroxide or urea perhydrate are dissolved in polyethylene oxides.

Moreover, it is preferred that the composition comprises at least one buffer substance, preferably a buffer substance from the group of primary alkali phosphates, secondary alkali phosphates, primary alkali citrates, secondary alkali citrates and/or a salt of carboxylic acids, in particular having 1 to 20 C atoms, preferably a salt of a fruit acid, a salt of an alpha-hydroxy acid and/or a salt of a fatty acid, in particular having 1 to 20 C atoms. Particularly preferred salts of the afore-mentioned acids are the alkali, alkaline earth and/or zinc salts of citric acid, malic acid, tartaric acid and/or lactic acid. Particularly preferred salts comprise the cations of sodium, potassium, magnesium and/or zinc of the afore-mentioned phosphates or carboxylates.

Accordingly, a salt, in particular a water-soluble salt, of a fruit acid, for example from the group of citric acid, malic acid, salicylic acid, tartaric acid, and lactic acid can be present in the antiseptic polymethylmethacrylate bone cement. Using this buffer substance in appropriate amounts allows the calcium hydroxide produced during hydrolysis of calcium peroxide to be neutralised. It is equally suitable to use alkali, alkaline earth, zinc salts of α-hydroxycarboxylic acids or fatty acids having 1 to 8 C atoms as buffer substances.

In this context, the buffer substance for controlling the pH and/or for controlling the release of hydrogen peroxide can be present together with the hydrogen peroxide compound i) as an adduct including a buffer substance, ii) in a co-crystal together with the buffer substance, iii) in a formulation together with at least one buffer substance, in particular as granulate, compactate, extrudate, in a matrix, a coated formulation, an enveloped pellet, or iv) in a mixture including at least one buffer substance, each optional in the presence of a further buffer substance and/or further customary pharmaceutical excipients and/or release-delaying coating agents.

According to another embodiment, the hydrogen peroxide compound can be embedded in or enveloped by an acrylate that can be swelled by $H_2O$ and is, in particular, pore-forming and eroding in order to control the delayed release kinetics even more strongly. EUDRAGIT® powder masses, for example, are typical delayed release acrylates.

It is particularly advantageous if the calcium peroxide and the buffer substance were granulated jointly and said granulates are added to the polymethylmethacrylate bone cement. The special advantage is that each grain of granulate contains a buffer substance that stabilises the pH during hydrolysis of the calcium peroxide. This all but prevents local alkaline reactions. The buffer substance content of the composition can be between 0.001 to 10% by weight, preferably from 0.001 to 5% by weight, particularly preferably from 0.001 to 2.5% by weight, even more preferably between 0.001 to 1% by weight, each relative to the total composition. In a formulation containing it jointly with the hydrogen peroxide compound, said concentration can be lower than when the hydrogen peroxide compound and buffer substance are simply mixed with the polymer and monomer.

The compositions according to the invention are bone cements comprising at least one organic polymer or mixtures of organic polymers, which are soluble, in particular, in the monomers, whereby the polymers are polyacrylates. The organic polymer is selected, in particular, from poly (alkyl-2-acrylic acid alkylester), poly(aryl-2-acrylic acid alkylester), poly(arylalkyl-2-acrylic acid alkylester), each independently having 1 to 18 C atoms in the alkyl group, in particular having 1 to 4 C atoms, each independently having 6 to 13 C atoms in the aryl group, in particular having 6, 10, 12 or 13 C atoms, each independently having 6 to 14 C atoms in the arylalkyl group, in particular having 8 to 12 C atoms, and each independently having 1 to 10 C atoms in the alkylester group, in particular having 1 to 4 C atoms, or a mixture comprising at least two of said polymers.

It is particularly preferred for the organic polymer, in particular a polymer that is soluble in the monomer, to be selected from the group of poly(methacrylic acid methylester), poly(methacrylic acid ethylester), poly(methylmethacrylic acid propylester), poly(methacrylic acid isopropylester), poly(methylmethacrylate-co-methylacrylate), poly (styrene-co-methylmethacrylate), copolymers of said compounds, and a mixture comprising at least two of said polymers, whereby polymethylmethacrylate (PMMA) is used particularly preferably.

A polymer that is soluble in the monomer for radical polymerisation shall be understood to be a polymer of which at least 10 g/l, preferably at least 25 g/l, more preferably at least 50 g/l, and even more preferably at least 100 g/l dissolve in said monomer for radical polymerisation. The polymer that is soluble in the polymerisable monomer can be a homopolymer or a copolymer. Said soluble polymer preferably is a polymer with a mean (by weight) molar mass (Mw) of at least 150,000 g/mol, in particular at least 200,000 g/mol and up to more than or equal to 5,000,000 g/mol. The soluble polymer can, for example, be a polymer or copolymer of a methacrylic acid ester. According to a particularly preferred embodiment, the at least one soluble polymer is selected from the group consisting of polymethacrylic acid methylester (PMMA), polymethacrylic acid ethylester (PMAE), polymethacrylic acid propylester (PMAP), polymethacrylic acid isopropylester, poly(methylmethacrylate-co-methylacrylate), poly(styrene-co-methylmethacrylate), and a mixture of at least two of said polymers.

The amount of the polymer that is soluble in said monomer for radical polymerisation that is present in the composition according to the invention usually is in a range of 1 to 85% by weight, relative to the total weight of the composition according to the invention. Accordingly, the polymer content of the following pastes A and/or B, and of powder component D and/or powder component C can, independent of each other, be 1 to 85% by weight relative to the respective total composition of paste, powder component or monomer component.

At least one poly(methacrylic acid methylester) (PMMA) and methacrylic acid methylester (MMA) are used as particularly preferred organic polymer and as monomer, respectively, whereby mixtures thereof including further monomers or a copolymer of PMMA can be used just as well.

Polymers, in particular polyacrylates, having a molecular weight (MW) of preferably more than or equal to 200,000 g/mol are used as polymers that are soluble in the monomers for producing powder components, whereby molecular weights of more than or equal to 500,000 g/mol are preferred. Polymers having a molecular weight of less than or equal to 500,000 g/mol can also be used in pastes. In this context, the suitable molecular weight is determined, on the one hand, by whether a paste or a powder component is being produced and by the further components present in the paste, and by the polymer having to be soluble in the monomer that is used.

The monomers for radical polymerisation used in the composition, inter alia in the monomer component or as monomer component, are preferably selected from at least one alkyl-2-acrylic acid alkylester, aryl-2-acrylic acid alkylester, arylalkyl-2-acrylic acid alkylester, each independently having 1 to 20 C atoms, preferably having 18 C atoms in the linear, branched or cyclic alkyl group, in particular having 1 to 4 C atoms, each independently having 6 to 13 C atoms in the aryl group, each independently having 6 to 14 C atoms in the arylalkyl group, in particular having 8 to 12 C atoms, and each independently having 1 to 20 C atoms in the alkylester group, preferably having 1 to 10 C atoms in the alkylester group, whereby the alkylester group can comprise a linear, branched or cyclic alkyl group, in particular having 1 to 4 C atoms, or be a mixture comprising at least two of said monomers, whereby methacrylic acid methylester, a methacrylic acid ester or an alkylacrylic acid methylester are preferred. Methacrylic acid methylester, such as a methacrylate monomer, in particular a methacrylate monomer that is liquid at a temperature of 25° C. and a pressure of 1,013 hPa, is particularly preferred. Preferably, the monomer for radical polymerisation is not a bisphenol A-derived methacrylic acid ester.

Preferably, the methacrylate monomer is a methacrylic acid ester. Preferably, the methacrylic acid ester is a monofunctional methacrylic acid ester. Preferably, said substance is hydrophobic. The use of hydrophobic monofunctional methacrylic acid esters allows later increases in bone cement volume due to the uptake of water and thus damage to the bone to be prevented. According to a preferred embodiment, the monofunctional methacrylic acid ester is hydrophobic if it contains no further polar groups aside from the ester group. The monofunctional hydrophobic methacrylic acid ester preferably comprises no carboxyl groups, hydroxyl groups, amide groups, sulfonic acid groups, sulfate groups, phosphate groups or phosphonate groups.

The monomer for radical polymerisation used according to the invention preferably has a molar mass of less than 1,000 g/mol. This also comprises monomers for radical polymerisation that are components of a mixture of monomers, whereby at least one of the monomers for radical polymerisation of the mixture of monomers has a defined structure with a molar mass of less than 1,000 g/mol.

The monomer for radical polymerisation is preferably characterised in that an aqueous solution, preferably one to which the monomer for radical polymerisation was added 1:1, has a pH in the range of 5 to 9, preferably in the range of 5.5 to 8.5, even more preferably in the range of 6 to 8, and particularly preferably in the range of 6.5 to 7.5.

According to a particularly preferred embodiment, the methacrylate monomer is methacrylic acid methylester, methacrylic acid ethylester or a mixture of said two monomers.

Preferably, the paste according to the invention contains an amount of the monomer for radical polymerisation in a range of 15 to 85% by weight, more preferably 20 to 70% by weight, even more preferably 25 to 60% by weight, and particularly preferably 25 to 50% by weight, each relative to the total weight of the paste according to the invention.

Also a subject matter of the invention are compositions comprising a particulate inorganic additive, in particular one having a BET surface of at least 40 m$^2$/g, whereby the additive preferably comprises covalently bound hydroxyl groups. Particulate inorganic additives that are suitable according to the invention comprise HO—Si groups that are covalently bound to the particles (silanol groups). Said hydroxyl groups that are arranged on the surface of the particles allow hydrogen bonds between the filling agent particles to form, which can be released reversibly through the action of mechanical or thermal energy.

The particulate inorganic additive is selected from the group of pyrogenic silicon oxide, pyrogenic mixed metal-silicon oxides, bentonite, montmorillonite, and a mixture containing at least two of said additives.

Moreover, it is also feasible to use pyrogenic silicon dioxide made hydrophobic. The hydrophobic silicon dioxide can be produced according to the prior art through treating pyrogenic silicon dioxide with dialkyldichlorosilanes (e.g. dimethyldichlorosilane).

Pyrogenic silicon dioxide with a BET surface of at least 40 m$^2$/g, particularly preferably of 200 m$^2$/g, and most preferably of 300 m$^2$/g, is particularly preferred as particulate inorganic filling agent. Said pyrogenic silicon dioxide is commercially available by the brand name of Aerosil® having specific BET surfaces of 50 m$^2$/g, 90 m$^2$/g, 200 m$^2$/g, and 380 m$^2$/g.

Pyrogenic silicon oxide having a BET surface of at least 200 m$^2$/g is particularly preferred. It is also preferred to use as particulate inorganic additive a pyrogenic silicon oxide having a BET surface of at least 300 m$^2$/g. The particulate inorganic additives that are suitable according to the invention preferably comprise primary particles of approx. 7 nm having a specific surface of 270 to 330 m$^2$/g.

The BET measurement is an analytical procedure for characterisation of the surface of solids by means of gas adsorption. Said determination method is described in DIN ISO 9277:2003-05 (Determination of the specific surface of solids by gas adsorption according to the BET method.

A composition according to the invention comprises, aside from the soluble organic polymer, in particular polymethylmethacrylate (PMMA), and the monomer for radical polymerisation, in particular methacrylic acid methylester, a particulate inorganic additive, preferably at a concentration from 0.01 to 0.5% by weight, in particular from 0.01 to 0.25% by weight, preferably from 0.02-0.14% by weight relative to the total composition. According to the invention, the cement dough produced by mixing the powder component and the liquid monomer component comprises the particulate inorganic additive at a concentration from 0.01-0.14% by weight. In addition to the components mentioned above, a composition according to the invention comprises a radiopaque material, a polymerisation initiator and/or a polymerisation accelerator and, optionally, additional filling agents other than the additive that simply possess a thickening effect.

Moreover, the composition can contain customary inorganic or organic filling agents, such as silicon dioxide having a BET surface of significantly less than 35 m$^2$/g.

According to an embodiment of the invention, a kit, preferably for producing a composition and/or bone cement according to the invention comprising a paste A and a paste B is disclosed, whereby
(a) paste A contains
(a1) at least one monomer for radical polymerisation, in particular at 15 to 85% by weight, preferably at 20 to 70% by weight, more preferably at 25 to 60% by weight, even more preferably at 25 to 50% by weight;
(a2) at least one organic polymer that is soluble in (a1), in particular at 5 to 50% by weight, preferably at 10 to 40% by weight, even more preferably at 20 to 30% by weight; and
(a3) at least one polymerisation initiator, in particular at 0.1 to 10% by weight, preferably at 0.01 to 8% by weight, even more preferably at 0.01 to 5% by weight, and, optionally, further ingredients, such as a radiopaque material and/or filling agent that is insoluble in (a1), each relative to the total weight of paste A; and
(b) paste B contains
(b1) at least one monomer for radical polymerisation, in particular at 15 to 85% by weight, preferably at 20 to 70% by weight, more preferably at 25 to 60% by weight, even more preferably at 25 to 50% by weight;
(b2) at least one organic polymer that is soluble in (b1), in particular at 5 to 50% by weight, preferably at 10 to 40% by weight, even more preferably at 20 to 30% by weight; and
(b3) at least one polymerisation accelerator, in particular at 0.0005 to 0.5% by weight, and, optionally, further ingredients, such as a radiopaque material and/or filling agent that is insoluble in (b1), each relative to the total weight of paste B, and whereby at least one of pastes A and B comprises as component (a4) or (b4) or both pastes A and B comprise as components (a4) and (b4) at least one content of a hydrogen peroxide compound, preferably from 0.001 to 10% by weight, more preferably from 0.001 to 5% by weight, particularly preferably from 0.001 to 2.5% by weight, even more preferably between 0.001 and 1% by weight, relative to the total composition of a paste.

In this context, each of the pastes can contain the particulate inorganic additive at a concentration of 0.001 to 2% by weight, in particular 0.001 to 1% by weight, such that 0.01 to 0.5% by weight of the additive, in particular from 0.01 to 0.25% by weight, preferably 0.02-0.14% by weight, relative to the total composition can be present in the composition that can be obtained through mixing pastes A and B at a ratio of approximately 1 to 1 (plus/minus 0.5 in either value).

The same applies in like manner to the following powder component C and paste D.

The monomers and polymers defined above are used as monomers and polymers in pastes A and B.

According to a further embodiment, a kit, preferably for producing a composition and/or bone cement according to the invention, comprising a powder component C and a monomer component D is disclosed, whereby the
(c) powder component C contains
(c1) at least one powder-shaped polyacrylate, in particular at 1 to 95% by weight, preferably up to 85% by weight;
(c2) at least one powder-shaped radiopaque material, in particular at 3 to 60% by weight, preferably 3 to 30% by weight; and
(c3) at least one polymerisation initiator, in particular at 0.1 to 10% by weight, preferably at 0.01 to 8% by weight, even more preferably at 0.01 to 5% by weight, and, optionally, further ingredients, such as a radiopaque material and/or filling agent that is insoluble in (a1), each relative to the total weight of powder component C;
and the
(d) monomer component D contains
(d1) at least one monomer for radical polymerisation, in particular at 90 to 99.9995% by weight;

(d2) optionally, at least one organic polymer that is soluble in (d1);
(b3) at least one polymerisation accelerator, in particular at 0.0005 to 0.5% by weight, and, optionally, further ingredients, such as a radiopaque material and/or filling agent that is insoluble in (d1), each relative to the total weight of monomer component D, and whereby at least powder component C or monomer component D comprises as component (c4) or (c4) or powder component C and monomer component D comprise as components (c4) and (d4) at least one content of a hydrogen peroxide compound, preferably from 0.001 to 10% by weight, more preferably from 0.001 to 5% by weight, particularly preferably from 0.001 to 2.5% by weight, even more preferably between 0.001 and 1% by weight, relative to one total composition of C or D.

In this context, it is preferable to use as hydrogen peroxide compound the aforementioned compounds, in particular hydrogen peroxide, hydrogen peroxide adducts, hydrogen peroxide complexes, hydrogen peroxide salts, hydrogen peroxide co-crystals, hydrogen peroxide-releasing compounds or mixtures containing at least two of the aforementioned compounds in one of the pastes A and/or B or, alternatively, in powder component C and/or monomer component D at the specified amounts, each relative to 100% by weight of the total composition.

Another subject matter of the invention is a kit containing a content of a buffer substance or of a mixture of buffer substances is present as component (a4) or (b5) in at least one of the pastes A or B or as component (a4) and (b5) in both pastes A and B. Also a subject matter of the invention is a kit containing a content of a buffer substance or of a mixture of buffer substances as component (c5) or (d5) in powder component C or monomer component D or as component (c5) and (d5) in both powder component C and monomer component D. The content of buffer substance can be between 0.001 to 10% by weight of the respective total composition of the pastes or of the monomer and powder components, preferably from 0.001 to 5% by weight, particularly preferably from 0.001 to 2.5% by weight, even more preferably between 0.001 to 1% by weight.

An organic polymer in the form of a powder according to the preceding definition is used as powder-shaped polyacrylate, whereby powder-shaped PMMA is preferred. In general, an additive content can be present both in the powder component and in the paste.

In the case of a composition according to the invention that was obtained by combining two pastes A and B or powder component C and monomer component D of a two-component system, said composition preferably contains at least one polymerisation initiator (that was present in the one paste/component of the two-component system) and at least one polymerisation accelerator (that was present in the other paste/component of the two-component system).

The monomers and polymers defined above are used as monomers and polymers in powder component C and monomer component D.

Usually, paste A and/or B and powder component C and/or monomer component D contain a radiopaque material, each independent of each other.

The above-mentioned pastes A and B can be mixed with each other at any arbitrary ratio, whereby the use of pastes A and B at a ratio of essentially 1:1 for mixing has proven to be preferred, whereby the ratio can vary by plus/minus 50% independent of each other.

The compositions, pastes and/or powder components according to the invention can contain at least one polymerisation initiator (which preferably is soluble in the monomer for radical polymerisation), at least one polymerisation accelerator (which preferably is soluble in the monomer for radical polymerisation), at least one co-polymerisation accelerator, if applicable, or at least one co-polymerisation initiator, if applicable.

In the case of a one-component system being the composition according to the invention, the polymerisation initiator preferably is an activatable polymerisation initiator, e.g. a photoinitiator that is dissolved or suspended in the composition, which is present as a paste, or a photoinitiator system that is dissolved or suspended in the paste. It is feasible just as well to provide an initiator or initiators where it/they are temporarily in contact with the paste, for example in a container part, a dosing facility or a transport cannula. Moreover, in a one-component system, the composition or paste according to the invention can also contain an electrically conductive radiopaque material aside from the activatable polymerisation initiator. Particles made of cobalt, iron, NdFeB, SmCo, cobalt-chromium steel, zirconium, hafnium, titanium, titanium-aluminium-silicon alloys, and titanium-niobium alloys having a particle size of 0.5-500 μm are particularly well-suited in this context. It is feasible to induce eddy currents in said electrically conductive radiopaque material through alternating magnetic fields of a frequency in the range of 500 Hz to 50 kHz which cause the radiopaque material to heat up. Due to heat transmission, the initiator is heated as well and induced to thermally disintegrate.

Also a subject matter of the invention is a curable bone cement that can be obtained by mixing pastes A and B or powder component C and monomer component D, as well as a cured bone cement that can be obtained by polymerising a composition according to the invention or can be obtained by mixing and polymerising pastes A and B or powder component C and monomer component D, whereby the bone cement comprises a content of hydrogen peroxide compound of more than or equal to 0.01% to 5% by weight, preferably from 0.01 to 1% by weight, relative to the total composition. Preferably, the hydrogen peroxide compound is released by delayed release from the curable or cured composition only in the presence of water, moist or aqueous conditions, particularly preferably only after curing.

Another subject matter of the invention is a cured bone cement, whereby a) the hydrogen peroxide compound as defined above preferably is a hydrogen peroxide adduct, a hydrogen peroxide complex, a hydrogen peroxide co-crystal or a hydrogen peroxide salt that releases hydrogen peroxide as compound having an oxidising effect in the presence of moisture, water, aqueous conditions or an aqueous solution, and/or b) is a hydrogen peroxide compound that releases hydrogen peroxide catalysed by enzymes, whereby the hydrogen peroxide is released by delayed release in a) and b).

Another subject matter of the invention is a form body that can be obtained through polymerisation of a composition according to the invention or by mixing pastes A and B or powder component C and monomer component D, and carrying out a polymerisation. It is also preferred in this context that the hydrogen peroxide compound in the cured form body releases hydrogen peroxide only upon contact to water, moisture or aqueous conditions, such as body fluid. Particularly preferably, the cured form body comprises 0.01 to 5% by weight of the hydrogen peroxide compound, relative to the total cured form body, such as preferably the at least one hydrogen peroxide adduct or hydrogen peroxide salt in the cured polymethylmethacrylate bone cement.

Another subject matter of the invention is the use of a composition according to the invention or of a kit according to the invention for producing an implant, an antiseptic implant, a revision implant, for mechanical fixation of primary total articular endoprostheses, for mechanical fixation of revision total articular endoprostheses, for augmentation of osteoporotic bone tissue and, particularly preferably, for vertebroplasty, kyphoplasty, and augmentation of drill holes in osteoporotic bone tissue, for filling bone cavities, for femuroplasty, for the manufacture of spacers, for mechanical fixation of articular endoprostheses, for covering skull defects or for the production of carrier materials for local antibiotics therapy or as carrier material for local release of pharmaceutically active substances.

Conceivable as polymerisation initiator are, in particular, peroxides and barbituric acid derivatives, whereby preferably at least 1 g/l, more preferably at least 3 g/l, even more preferably at least 5 g/l, and particularly preferably at least 10 g/l of the peroxides and barbituric acid derivatives can dissolve(s) in the polymerisable monomer at a temperature of 25° C. The polymerisation initiators disintegrate through radical reactions, usually while forming hydrogen radicals and cleaving off oxygen. The initiator does not form hydrogen peroxide in the presence of water. Cumene hydroperoxide can become rearranged in the presence of water to form ketone and phenol. Radicals such as H—O—O., R—O—O., R=organic residue, are not considered to be hydrogen peroxide.

According to the invention, a peroxide is understood to mean compounds that contain at least one peroxo group (—O—O—). The peroxide preferably comprises no free acid groups. The peroxide can be an inorganic peroxide or an organic peroxide, such as, for example, a toxicologically acceptable hydroperoxide. However, the hydroperoxide is not a hydrogen peroxide. According to a particularly preferred embodiment, the peroxide is selected from the group consisting of cumene-hydroperoxide, 1,1,3,3-tetramethyl-butylhydroperoxide, t-butyl-hydroperoxide, t-amyl-hydroperoxide, di-isopropylbenzen-mono-hydroperoxide, and a mixture of at least two of these substances.

The barbituric acid derivative preferably is a barbituric acid derivative selected from the group consisting of 1-mono-substituted barbiturates, 5-mono-substituted barbiturates, 1,5-di-substituted barbiturates, and 1,3,5-tri-substituted barbiturates. According to a particular refinement of the paste according to the invention, the barbituric acid derivative is selected from the group consisting of 1,5-di-substituted barbiturates and 1,3,5-tri-substituted barbiturates.

There is no limitation with regard to the type of substituents on the barbituric acid. The substituents can, for example, be aliphatic or aromatic substituents. In this context, alkyl, cycloalkyl, allyl or aryl substituents can be preferred. The substituents can also include hetero atoms. In particular, the substituents can be thiol substituents. Accordingly, 1,5-disubstituted thiobarbiturates or 1,3,5-trisubstituted thiobarbiturates can be preferred. According to a preferred embodiment, the substituents each have a length of 1 to 10 carbon atoms, more preferably a length of 1 to 8 carbon atoms, and particularly preferably a length in the range of 2 to 7 carbon atoms. According to the invention, barbiturates bearing one substituent each at position 1 and position 5 or a substituent at positions 1, 3, and 5 are preferred. According to another preferred embodiment, the barbituric acid derivative is a 1,5-disubstituted barbiturate or a 1,3,5-trisubstituted barbiturate. According to a particularly preferred embodiment, the barbituric acid derivative is selected from the group consisting of 1-cyclohexyl-5-ethyl-barbituric acid, 1-phenyl-5-ethyl-barbituric acid, and 1,3,5-trimethyl-barbituric acid.

Heavy metal compounds selected from the group consisting of heavy metal salts and heavy metal complexes are preferred as polymerisation accelerator. Heavy metal compounds that are preferred according to the invention are selected from the group consisting of copper(II) hydroxide, copper(II) methacrylate, copper(II) acetylacetonate, copper (II)-2-ethyl-hexanoate, cobalt(II) hydroxide, cobalt(II)-2-ethyl-hexanoate, basic copper(II) carbonate, iron(II)-2-ethyl-hexanoate, iron(III)-2-ethyl-hexanoate, and a mixture of at least two of these substances.

According to another refinement of the composition or paste according to the invention, the polymerisation accelerator is selected from the group consisting of N,N-dimethyl-p-toluidine, N,N-bis-hydroxyethyl-p-toluidine, N,N-dimethyl-aniline, trioctylmethylammoniumchloride, tetrabutylammoniumchloride, lithium chloride, saccharin, 1,8-diazabicyclo[5.4.0]undec-7-ene, and 1,5-diazabicyclo(4.3.0)non-5-ene, phthalimide, maleimide, succinimide, pyromellitic acid diimide, and a mixture of at least two of these substances.

Another advantageous refinement of the invention comprises the use, as polymerisation accelerator, of combinations of heavy metal salts and at least one member of the group comprising N,N-dimethyl-p-toluidine, N,N-bis-hydroxyethyl-p-toluidine, N,N-dimethyl-aniline, trioctylmethylammoniumchloride, tetrabutylammoniumchloride, lithium chloride, saccharin, 1,8-diazabicyclo[5.4.0]undec-7-ene, and 1,5-diazabicyclo(4.3.0)non-5-ene, phthalimide, maleimide, succinimide, and pyromellitic acid diimide. Combinations of two and combinations of three different polymerisation accelerators in this context are disclosed in the scope of the invention.

An advantageous refinement of the invention is that the composition according to the invention or any of the pastes A, B or monomer component D contains at least one copolymerisation accelerator, if applicable, whereby tertiary amines and amidines are preferred as polymerisation co-accelerators, and whereby N,N-dimethyl-p-toluidine, N,N-bis-hydroxyethyl-p-toluidine, N,N-dimethyl-aniline, 1,8-diazabicyclo[5.4.0-]undec-7-ene, and 1,5-diazabicyclo(4.3.0)-non-5-ene are particularly preferred as co-accelerators.

The composition according to the invention, in particular in a paste or monomer component, can contain a (total) amount of the polymerisation initiator, polymerisation accelerator, co-polymerisation accelerator or the polymerisation initiator, polymerisation accelerator, and co-polymerisation accelerator of up to 10% by weight, relative to the total weight of the composition according to the invention or, each independent of each other, relative to the total weight of any of the pastes A, B or monomer component D.

The composition according to the invention and, in particular, the pastes A and B as well as monomer component D and powder component C can contain further ingredients aside from the afore-mentioned components.

According to a preferred embodiment of the composition according to the invention or of any of the pastes A, B and monomer component D or powder component C, these can, each independent of each other, contain at least one radiopaque material. The radiopaque material can be a common radiopaque material in this field. Suitable radiopaque materials can be soluble or insoluble in the monomer for radical polymerisation. The radiopaque material is preferably selected from the group consisting of metal oxides (such as, for example, zirconium oxide), barium sulfate, toxicologically acceptable heavy metal particles (such as, for example, tantalum), ferrite, magnetite (supramagnetic magnetite also, if applicable), and biocompatible calcium salts. Said radiopaque materials preferably have a mean particle diameter in the range of 10 nm to 500 µm. Moreover, conceivable radiopaque materials also include esters of 3,5-bis(acetamido)-2,4,6-triiodobenzoic acid, gadolinium compounds, such as gadolinium chelate involving the esters of 1,4,7,10-tetraazacyclododecan-1,4,7,10-tetraacetic acid (DOTA). The radiopaque material concentrations, in particular the zirconium dioxide concentration, in the composition according to the invention or any of the pastes A or B and powder component C or monomer component D can, each independent of each other, be in a range of, for example, 3 to 30% by weight relative to the corresponding total composition. Radiopaque materials are not considered to be filling agents herein.

According to a further preferred embodiment, the composition according to the invention or any of the pastes specified above can contain at least one colourant. The colourant can be a common colourant in this field and preferably can be a food colourant. Moreover, the colourant can be soluble or insoluble in the at least one monomer for radical polymerisation. According to a particularly preferred embodiment, the colourant is selected from the group consisting of E101, E104, E132, E141 (chlorophyllin), E142, riboflavin, and lissamine green. According to the invention, the term, colourant, shall also include colour varnishes, such as, for example, colour varnish green, the aluminium salt of a mixture of E104 and E132.

According to a further preferred embodiment, the composition according to the invention can contain at least one biocompatible elastomer. Preferably, the biocompatible elastomer is particulate. Preferably, the biocompatible elastomer is soluble in the at least one monomer for radical polymerisation. The use of butadiene as biocompatible elastomer has proven to be particularly well-suited.

According to a further preferred embodiment, the composition according to the invention can contain at least one monomer having adsorption groups. An adsorption group can, for example, be an amide group. Accordingly, the monomer with adsorption group can, for example, be methacrylic acid amide. Using at least one monomer with adsorption groups would allow the binding of the bone cement to articular endoprostheses to be influenced in a targeted manner.

According to a further preferred embodiment, the composition according to the invention or at least one of the pastes A, B or monomer component D can contain at least one stabiliser. The stabiliser should be suitable to prevent spontaneous polymerisation of the monomers for radical polymerisation that are contained in the paste. Moreover, the stabiliser should not undergo interfering interactions with the other ingredients contained in the paste according to the invention. Stabilisers of said type are known according to the prior art. According to a preferred embodiment, the stabiliser is 2,6-di-tert-butyl-4-methylphenol and/or 2,6-di-tert-butyl-phenol.

According to the invention, a kit shall be understood to be a system made up of at least two components. Although reference to two components (e.g. paste A and paste B) is made in the following, the kit can just as well contain more than two components, for example three, four, five or more than five components, according to need. The individual components preferably are provided to be packaged separate from each other such that the ingredients of the one kit component do not contact the ingredients of another kit component. Accordingly, it is feasible, for example, to package the respective kit components separate from each other and to store them together in a reservoir container.

Preferably, the kit is designed as a device for producing compositions for use as bone cement in appropriate manner such that it comprises a first container and a second container, whereby the first container comprises, for example, paste A and the second container comprises paste B, whereby at least one of the containers can be opened to allow paste A and paste B to be mixed after the opening, and a mixing unit for the mixing of pastes A and B. Accordingly, the kit as a device for producing the composition according to the invention can comprise a first container for powder component C and a second container for monomer component D.

Referring to the first kit, for this purpose, the at least two pastes A and B are mixed with each other, upon which the composition according to the invention is obtained. The mixing ratio preferably is 0.5 to 1.5 parts by weight of paste A and 0.5 to 1.5 parts by weight of paste B. According to a particularly preferred embodiment, the fraction of paste A is 30 to 70% by weight and the fraction of paste B is 30 to 70% by weight, each relative to the total weight of pastes A and B, respectively. The mixing ratio of powder component C and monomer component D preferably is 3:1 to 1:3, in particular 2:2 party by weight. The mixing process can involve common mixing devices, for example a static mixer or a dynamic mixer.

After the pastes of the kit are mixed, the composition that is ultimately obtained is tack-free in accordance with the ISO 5833 standard after no more than 1 to 2 minutes.

The antiseptic polymethylmethacrylate bone cement according to the invention can be used as cement for mechanical fixation of primary total articular endoprostheses, for mechanical fixation of revision total articular endoprostheses, and for producing spacers.

The invention is illustrated in more detail through the examples presented in the following, though without limiting the scope of the invention.

The following examples were implemented using Palacos® R cement powder (batch no. B7457), a PMMA cement powder. Urea-peroxide adduct and calcium peroxide were procured from Sigma-Aldrich.

In each case, 10.0 g Palacos® R cement powder and finely powdered urea-peroxide adduct or calcium peroxide were weighed and placed in 100 ml plastic vessels with screw caps and then mixed for 30 minutes in a Turbula mixer. The composition of examples 1-9 is listed in the two tables below.

Subsequently, the mixtures were each mixed with 5 ml Palacos® monomer liquid, which is a monomer liquid. A tack-free cement dough was formed within 60 seconds. Said cement dough was then pasted into cylindrical plastic moulds. The cylindrical test bodies (height 12 mm, diameter 6 mm) were removed after the curing process was completed.

| | Cement powder composition | |
|---|---|---|
| Examples | Palacos ® R cement powder [g] | Urea-peroxide adduct [g] |
| 1 | 10.0 | 1.50 |
| 2 | 10.0 | 1.00 |
| 3 | 10.0 | 0.75 |
| 4 | 10.0 | 0.50 |
| 5 | 10.0 | 0.25 |

| Examples | Cement powder composition | |
|---|---|---|
|  | Palacos ® R cement powder [g] | Calcium peroxide[g] |
| 6 | 10.0 | 1.00 |
| 7 | 10.0 | 0.50 |
| 8 | 10.0 | 0.25 |

For a reference (example 10), pure Palacos® R powder was mixed with 5 ml monomer liquid and cylindrical test bodies (height 12 mm, diameter 6 mm) were produced in this case as well.

The test bodies were tested for their antimicrobial activity by QualityLabs BT GmbH Nuremberg (Report Measurement 20120807-RB01-10). MRSA test strain *Staphylococcus aureus* DSM 21979/EDCC 5247 was used as test pathogen in the tests. The test of antimicrobial efficacy was carried out in accordance with the SOP for *Staphylococcus epidermidis*, SOP 3.2 from 2008-08-05 using the MRSA test strain, *Staphylococcus aureus*. The Certika proliferation test was carried out. The test bodies were first incubated in bacterial suspension for this purpose. Subsequently, the test bodies were washed and then incubated for 18 hours in fresh nutrient medium at 37° C. Then, a 200 µl aliquot was taken and transferred to a micro-titre plate. The optical density was then measured every 30 minutes for a period of 48 hours. The optical density increases as a function of time if there is microbial growth. The aim was to detect the proliferation of the bacterium on the test surface.

The aliquots from the test bodies of examples 1-9 showed no growth at all of the test pathogen over the 48 hour period, as is shown in the table below. The bacteria could not proliferate in the surrounding medium at 37° C. in a period of more than or equal to 48 hours, and did not produce daughter cells. This means that the test bodies have a pronounced antimicrobial effect.

In contrast, the eluates of the reference test bodies of example 10 did not impede the growth of the test pathogen.

| Example | Onset OD [h] | Onset OD [h] | Standard deviation | CV [%] | Result |
|---|---|---|---|---|---|
| Reference test body | 12.6 | — | 1.2 | 9.3 |  |
| 1 | >48.0 | >48.0 | 0.0 | 0.0 | antimicrobial |
| 2 | >48.0 | >48.0 | 0.0 | 0.0 | antimicrobial |
| 3 | >48.0 | >48.0 | 0.0 | 0.0 | antimicrobial |
| 4 | >48.0 | >48.0 | 0.0 | 0.0 | antimicrobial |
| 5 | >48.0 | >48.0 | 0.0 | 0.0 | antimicrobial |
| 6 | >48.0 | >48.0 | 0.0 | 0.0 | antimicrobial |
| 7 | >48.0 | >48.0 | 0.0 | 0.0 | antimicrobial |
| 8 | >48.0 | >48.0 | 0.0 | 0.0 | antimicrobial |

The invention claimed is:

1. Composition for use as a bone cement, said composition comprising a curable mixture comprising: (A) at least one organic polymer selected from the group consisting of polyacrylates (B) at least one hydrogen peroxide salt that releases hydrogen peroxide as a compound having an oxidizing effect in the presence of moisture, water, aqueous conditions or an aqueous solution; and (c) at least one polymerisation initiator; wherein the composition does not comprise stabilizers.

2. Composition according to claim 1, wherein the hydrogen peroxide salt is a calcium peroxide, calcium peroxide-octahydrate, and/or sodium peroxide.

3. Composition according to claim 1, wherein the composition contains 0.01 to 10% by weight of the hydrogen peroxide salt.

4. Composition according to claim 1, wherein the composition comprises at least one buffer substance.

5. Composition according to claim 4, wherein the composition comprises at least one buffer substance or a mixture of buffer substances selected from the group consisting of alkali phosphates, and alkali, alkaline earth and/or zinc salts of carboxylic acids having 1 to 20 C atoms.

6. Composition according to claim 4, wherein the composition comprises at least one buffer substance selected from the group consisting of alkali, alkaline earth and/or zinc salts of alpha-hydroxy acids having at most 20 C atoms, fatty acids having at most 20 C atoms, citric acid, malic acid, tartaric acid, and lactic acid.

7. Composition according to claim 1, wherein the hydrogen peroxide salt is present i) as an adduct including a buffer substance, ii) in a co-crystal together with a buffer substance, or iii) in a formulation together with at least one buffer substance.

8. Composition according to claim 1, wherein the at least one organic polymer is polymethylmethacrylate.

9. Composition according to claim 1, wherein the composition comprises at least one monomer for radical polymerisation and the at least one organic polymer is soluble in said monomer.

10. Composition according to claim 1, wherein the composition further comprises inorganic particles comprising hydroxyl groups covalently bonded thereto.

11. Composition according to claim 1, wherein the at least one organic polymer is selected from poly(alkyl-2-acrylic acid alkylester), which has 1 to 20 C atoms in the alkyl group and 1 to 10 C atoms in the alkylester group; poly(aryl-2-acrylic acid alkylester), which has 6 to 14 C atoms in the aryl group and 1 to 10 C atoms in the alkylester group; and poly(arylalkyl-2-acrylic acid alkylester), which has 6 to 14 C atoms in the arylalkyl group and 1 to 10 C atoms in the alkylester group; or a mixture comprising at least two of said polymers.

12. Composition according to claim 9, wherein the at least one organic polymer is selected from the group of poly(methacrylic acid methylester), poly(methacrylic acid ethylester), poly(methylmethacrylic acid propylester), poly(methacrylic acid isopropylester), poly(methylmethacrylate-co-methylacrylate), poly(styrene-co-methylmethacrylate), copolymers of said compounds, and a mixture of at least two of said polymers.

13. Composition according to claim 8, which further comprises at least one curable monomer, wherein the monomer is selected from at least one alkyl-2-acrylic acid alkylester, which has 1 to 20 C atoms in the alkyl group and 1 to 10 C atoms in the alkylester group; aryl-2-acrylic acid alkylester, which has 6 to 14 C atoms in the aryl group and 1 to 10 C atoms in the alkylester group; and arylalkyl-2-acrylic acid alkylester, which has 6 to 14 C atoms in the arylalkyl group and 1 to 10 C atoms in the alkylester group; or a mixture comprising at least two of said monomers.

14. Composition according to claim 8, which further comprises methacrylic acid methylester (MMA) monomer, and wherein the at least one organic polymer comprises at least one poly(methacrylic acid methylester), (PMMA).

15. Cured bone cement obtained by a process comprising polymerising a composition according to claim 1, whereby the bone cement comprises a content of hydrogen peroxide salt of 0.01 to 5% by weight, relative to the total composition.

16. Form body obtained by polymerising a composition according to claim 1.

17. Kit comprising a paste A and a paste B, whereby
(a) paste A comprises:
(a1) at least one monomer for radical polymerisation;
(a2) at least one organic polymer that is soluble in (a1); and
(a3) at least one polymerisation initiator;
(b) paste B comprises:
(b1) at least one monomer for radical polymerisation;
(b2) at least one organic polymer that is soluble in (b1); and
(b3) at least one polymerisation accelerator;
whereby at least one of the pastes A and/or B comprises a hydrogen peroxide salt as component (a4) and/or (b4), whereby the hydrogen peroxide salt releases hydrogen peroxide as a compound having an oxidizing effect in the presence of moisture, water, aqueous conditions or an aqueous solution, and wherein the kit does not comprise stabilizers.

18. Curable bone cement obtained by a process comprising providing a kit according to claim 17 and mixing pastes A and B.

19. Form body obtained by a process comprising providing a kit according to claim 17, mixing pastes A and B present in the kit, and polymerizing.

20. Kit, comprising a powder component C and a monomer component D, whereby the
(c) powder component C comprises:
(c1) at least one polyacrylate powder;
(c2) at least one radiopaque powder; and
(c3) at least one polymerisation initiator;
(d) monomer component D comprises:
(d1) at least one monomer for radical polymerisation;
(d2) optionally, at least one organic polymer that is soluble in (d1); and
(d3) at least one polymerisation accelerator;
whereby at least powder component C and/or monomer component D comprise(s) a hydrogen peroxide salt as component (c4) and/or (d4), whereby the hydrogen peroxide salt releases hydrogen peroxide as a compound having an oxidizing effect in the presence of moisture, water, aqueous conditions or an aqueous solution, and wherein the kit does not comprise stabilizers.

21. Curable bone cement obtained by a process comprising providing a kit according to claim 20 and mixing powder component C and monomer component D.

22. Form body obtained by a process comprising providing a kit according to claim 20, mixing powder component C and monomer component D present in the kit, and polymerizing.

23. A composition for use as a bone cement, wherein the composition is curable, and the composition comprises: (a) at least one polyacrylate polymer; (b) at least one polymerizable acrylate monomer, wherein (a) is soluble in (b); (c) at least one hydrogen peroxide salt that releases hydrogen peroxide when contacted with a bodily fluid; and (d) at least one polymerisation initiator; wherein the composition does not comprise stabilizers.

24. A cured bone cement comprising: (a) at least one polyacrylate polymer; and (b) at least one hydrogen peroxide salt that releases hydrogen peroxide when contacted with a bodily fluid, wherein the cured bone cement does not comprise stabilizers.

25. A method of augmenting osteoporotic bone tissue, said method comprising applying a composition according to claim 1 into said bone tissue.

26. A method conducted for a purpose selected from: mechanical fixation of primary total articular endoprostheses, mechanical fixation of revision total articular endoprostheses, augmentation of osteoporotic bone tissue, vertebroplasty, kyphoplasty, augmentation of drill holes in osteoporotic bone tissue, filling bone cavities, femuroplasty, manufacture of spacers, mechanical fixation of articular endoprostheses, covering skull defects and as carrier materials for local antibiotics therapy or for local release of pharmaceutically active substances, said method comprising introducing a composition according to claim 1 into a patient's body for said purpose.

27. A method of combating local infection by microorganisms at a site of implantation of a bone cement into a patient during and after the introduction of a bone cement into the patient's body, said method comprising introducing into the patient's body as the bone cement the composition according to claim 1 and curing the composition, wherein the hydrogen peroxide salt in said composition, once the composition is introduced into the patient's body, contacts body fluid of the patient liberating hydrogen peroxide thereby combating said infection by said microorganisms.

28. A method of combating local infection by microorganisms at a site of implantation of a bone cement into a patient during and after the introduction of a bone cement into the patient's body, said method comprising introducing into the patient's body as the bone cement the composition according to claim 23 and curing the composition, wherein the hydrogen peroxide salt in said composition, once the composition is introduced into the patient's body, contacts body fluid of the patient liberating hydrogen peroxide thereby combating said infection by said microorganisms.

* * * * *